Dec. 24, 1957 R. V. LINDQUIST Plant Pat. 1,671
ROSE PLANT
Filed April 29, 1957
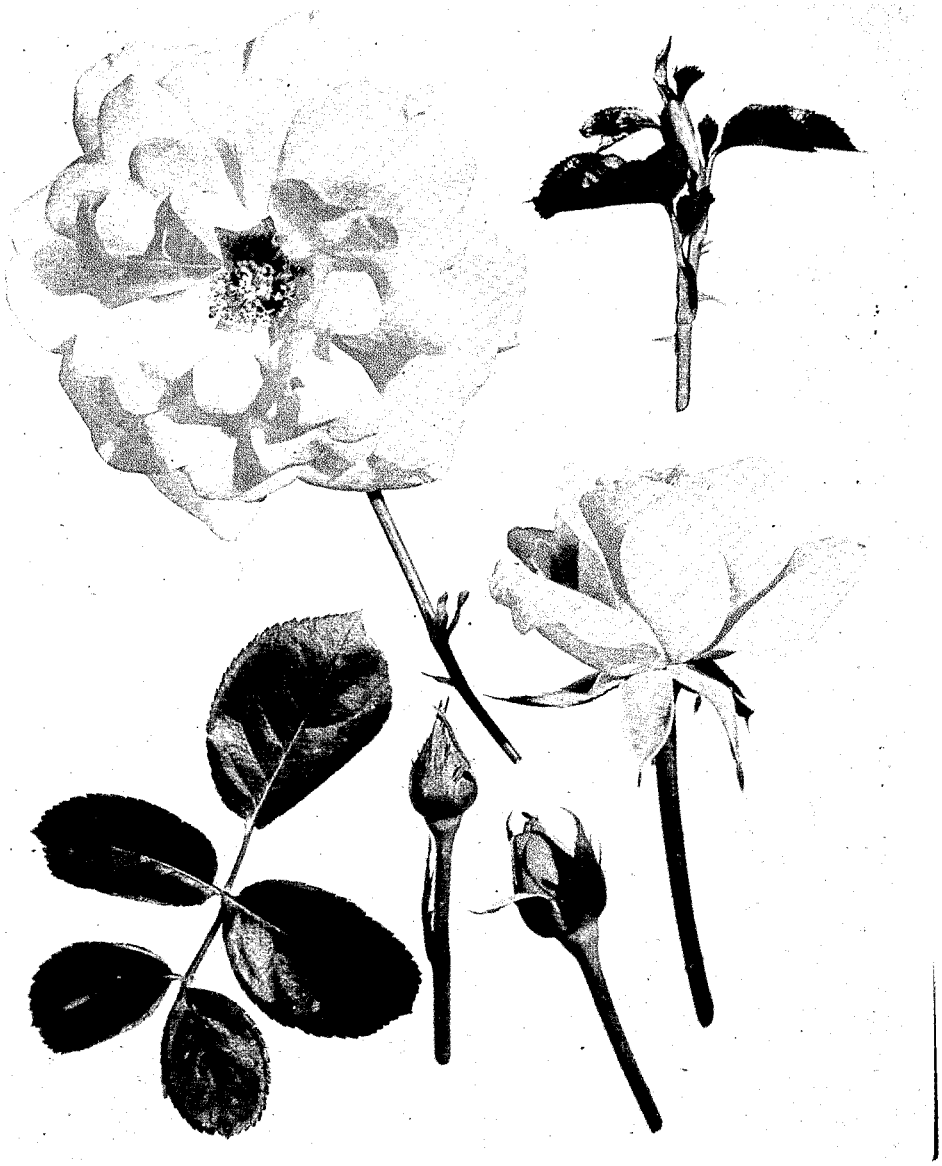
Inventor.
R. V. Lindquist
By: Robb & Robb
Attorneys United States Patent Office Plant Pat. 1,671
Patented Dec. 24, 1957

1,671

ROSE PLANT

Robert V. Lindquist, Hemet, Calif., assignor to Hemet Wholesale, Hemet, Calif., a partnership Application April 29, 1957, Serial No. 655,929

1 Claim. (Cl. 47—61)

The present invention relates to a new and distinct variety of rose plant of the hybrid polyantha class, which was originated by me by crossing the variety known as "Improved Lafayette" (unpatented) with the variety "Floradora" (unpatented).

As the result of this breeding, I have produced a new rose variety which is particularly characterized as to novelty by the distinctive and unique color of its new foliage, and the distinctive color of its flowers, as hereinafter more fully described. These characteristics and distinctions definitely differentiate the new variety from its parents, as well as from all other varieties of its class of which I am aware.

Asexual reproduction of my new variety by budding, as performed at Hemet, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Ridgway's Color Standards and Nomenclature (hereinafter abbreviated as "Ridgway"), as indicated, except where color terms of ordinary dictionary significance are obvious:

Type: Bush; outdoor; seedling; for garden decoration.
Class: Hybrid Polyantha.
Breeding: Seedling.
*Seed parent.*—"Improved Lafayette."
*Pollen parent.*—"Floradora."
Propagation: Holds its distinguishing characteristics through succeeding propagations by budding.

*Flower*

Locality where grown and observed: Hemet, California.
Flowers borne: Usually three to five to stem; in irregular, flat clusters; on strong stems of medium length.
Quantity of bloom: Very free, outdoors.
Continuity: Continuous during growing season.
Fragrance: Slight. Nature—spicy.
Bud:
*Peduncle.*—Average length; average caliper; erect; moderately smooth; few gland-tipped cilia; few prickles. Color—near Biscay Green, Plate XVII (Ridgway).
*Before calyx breaks.*—Size—medium. Form—medium length; pointed; with foliaceous appendages on the surface of the bud; with few gland-tipped cilia and glandular bloom on the surface of the bud; usually with slender, bristle-like parts extending beyond the tip of the bud equal to ¼ or more of its length.

*As calyx breaks.*—Color—near China Rose, Plate 024, page 111 (Wilson).
*Sepals.*—Inner surface—with fine, wooly tomentum. Margin—with gland-tipped cilia.
*As first petal opens.*—Size—average. Form—medium length; ovoid. Color: outside—near China Rose, Plate 024/1, page 111 (Wilson), with base near Primrose Yellow, Plate 601/3, page 65 (Wilson); inside—near Neyron Rose, Plate 623/1, page 76 (Wilson), with base near Primrose Yellow, Plate 601/3, page 65 (Wilson).
*Opening.*—Opens up well; is not retarded from opening by cold, hot, wet or dry weather.
Bloom:
*Size (when fully open).*—Average; from three inches to three-and-a-half inches.
*Petalage.*—Double; from 23 to 27 petals, plus 5 to 8 pentaloids; arranged irregularly.
*Form.*—From flat to high-centered at first, but becoming flat to open; petals being at first somewhat cupped, with tips rolled outward, and becoming somewhat flat, with tips rolled outward, later at maturity.
Petals:
*Texture.*—Medium.
*Appearance.*—Inside—satiny. Outside—from slightly shiny to satiny.
*Shape.*—Outside—round, with apex flat. Intermediate—oval, with apex flat. Inside—nearly oval, with apex flat.

This description of a newly opened flower was made from a rose grown outdoors in the month of September, at Hemet, California:

*Color.*—Outer petal: outside surface—near Tyrian Rose, Plate 24/2, page 24 (Wilson), with base near Primrose Yellow, Plate 601/3, page 65 (Wilson); inside surface—near Neyron Rose, Plate 623/1, page 76 (Wilson), with base near Primrose Yellow, Plate 601/3, page 65 (Wilson). Intermediate petal: outside surface—near Tyrian Rose, Plate 24/2, page 24 (Wilson), with base near Primrose Yellow, Plate 601/3, page 65 (Wilson); inside surface—near Neyron Rose, Plate 623/1, page 76 (Wilson), with base near Primrose Yellow, Plate 601/3, page 65 (Wilson). Inner petal: outside surface—near Tyrian Rose, Plate 24/2, page 24 (Wilson), with base near Primrose Yellow, Plate 601/3, page 65 (Wilson); inside surface—near Neyron Rose, Plate 623/1, page 76 (Wilson), with base near Primrose Yellow, Plate 601/3, page 65 (Wilson).

This description was made from a rose that was open for three days outdoors in the month of September, at Hemet, California:

*Color.*—Outer petal: outside surface—near Tyrian Rose, Plate 24/2, page 24 (Wilson), with base near Primrose Yellow, Plate 601/3, page 65 (Wilson); inside surface—near Rose Bengal, Plate 25/2, page 25 (Wilson), with base near Primrose Yellow, Plate 601/3, page 65 (Wilson). Inner petal: outside surface—near Tyrian Rose, Plate 24/2, page 24 (Wilson), with base near Primrose Yellow, Plate 601/3, page 65 (Wilson); inside surface—near Rose Bengal, Plate 25/1, page 25 (Wilson), with base near Primrose Yellow, Plate 601/3, page 65 (Wilson).
*General color effect.*—Newly opened flower—near Neyron Rose, Plate 623/1, page 76 (Wilson). Three days open—near Neyron Rose, Plate 623/1, page 76 (Wilson).

*Behavior.*—Drop off cleanly.

*Flower longevity.*—On bush in garden—from 2 to 4 days in September. Cut roses grown outdoors and kept at livingroom temperatures—two or three days in September.

*Reproductive organs*

Stamens: Average number; arranged regularly about pistils.

Filaments: Medium length; most with anthers. Color—near China Rose, Plate 024/1, page 111 (Wilson), at base, shading to near China Rose, Plate 024/3, page 111 (Wilson).

Anthers: Medium size; all open approximately at once. Color: upper side—near Ochraceous Buff, Plate XV (Ridgway); under side—near Ochraceous Buff, Plate XV (Ridgway).

Pollen: Moderate. Color—near Straw Yellow, Plate 604, page 67 (Wilson).

Pistils: Average number; approximately 75 in number.

Styles: Moderately even; average length; thin; somewhat bunched.

Stigma: color—near Orange Buff, Plate 507/2, page 133 (Wilson).

Ovaries: Usually most enclosed in calyx, but some protruding from calyx.

Hips: None.

Sepals: Falling soon; moderately long. Color: inside—near Pale Fluorite Green, Plate XXXII (Ridgway); outside—near Light Bice Green, Plate XVII (Ridgway).

Seeds: None.

*Plant*

Foliage:

*Leaves.*—Compound of usually three to five leaflets; abundant; medium size; moderately heavy; semi-glossy.

*Leaflets.*—Shape—oval, with apex mucronate. Base—obtuse. Margin—irregularly serrate.

*Color.*—Mature: upper surface—near Dark Yellowish Green, Plate XVIII (Ridgway), with some shadings of near Nickel Green, Plate XXXIII (Ridgway); under surface—near Chromium Green, Plate XXXII (Ridgway). Young: upper surface—near Cedar Green, Plate VI (Ridgway) at center of leaf, shading to near Dark Corinthian Purple, Plate XXXVIII (Ridgway); under surface—near Dark Corinthian Purple, Plate XXXVIII (Ridgway).

*Rachis (the supporting stem of the compound leaf).*—Average size. Upper side—grooved; with some stipitate glands on edges and with some prickles. Under side—moderately prickly; with few stipitate glands.

*Stipules.*—Medium length; medium width; with medium length points turning out at an angle of about 45°.

*Disease resistance.*—Mildly subject to mildew, as determined by comparison with other varieties grown under comparable cultural conditions at Hemet, California.

Growth:

*Habit.*—Bushy; upright; moderately branched.

*Growth.*—Vigorous.

*Canes.*—From medium caliper to heavy.

*Main stems.*—Color—near Oil Green, Plate V (Ridgway). Large prickles—several; from medium length to long; hooked slightly downward; with medium length, moderately narrow base; color—near Russet, Plate XV (Ridgway). Small prickles—none. Hairs—none.

*Branches.*—Color—near Spinach Green, Plate V (Ridgway), with occasional shadings of Corinthian Purple, Plate XXXVIII (Ridgway). Large prickles—several; medium length; hooked slightly downward; with medium length, moderately narrow base; color—near Russet, Plate XV (Ridgway). Small prickles—none. Hairs—none.

*New shoots.*—Color—near Dark Corinthian Purple, Plate XXXVIII (Ridgway), with occasional areas of near Chromium Green, Plate XXXII (Ridgway). Larke prickles—several; medium length; hooked slightly downward; with medium length, moderately narrow base; color—near Corinthian Purple, Plate XXVIII (Ridgway). Small prickles—few. Hairs—none.

I claim:

A new and distinct variety of rose plant of the hybrid polyantha class, substantially as herein shown and described, characterized particularly as to novelty by the distinctive and unique color of its new foliage, and the distinctive color of its flowers.

No references cited.